US005828770A

United States Patent [19]
Leis et al.

[11] Patent Number: 5,828,770
[45] Date of Patent: Oct. 27, 1998

[54] SYSTEM FOR DETERMINING THE SPATIAL POSITION AND ANGULAR ORIENTATION OF AN OBJECT

[75] Inventors: Stephen Eldon Leis, Waterloo; David Ristau, Kitchener, both of Canada

[73] Assignee: Northern Digital Inc., Ontario, Canada

[21] Appl. No.: 603,791

[22] Filed: Feb. 20, 1996

[51] Int. Cl.$^6$ ..................................................... G06K 9/00
[52] U.S. Cl. ........................................... 382/103; 382/154
[58] Field of Search .................................... 382/103, 151, 382/153, 154, 291; 348/47, 77, 87, 94, 95, 169, 172, 139; 901/47; 364/559; 250/203.3, 559.33, 559.29, 206.2; 395/105, 173, 94, 358; 356/375; 345/158

[56] References Cited

U.S. PATENT DOCUMENTS

| | | | |
|---|---|---|---|
| 4,396,945 | 8/1983 | DiMatteo et al. | 348/139 |
| 4,649,504 | 3/1987 | Krouglicof et al. | 364/559 |
| 5,227,985 | 7/1993 | DeMenthon | 364/559 |
| 5,530,771 | 6/1996 | Maekawa | 382/103 |

FOREIGN PATENT DOCUMENTS

| | | |
|---|---|---|
| 1 307 663 | 9/1992 | Canada . |
| 1 164 726 | 10/1979 | Italy . |
| 1 380 537 | 7/1973 | United Kingdom . |

OTHER PUBLICATIONS

Kazvo Hemmi & Kazuo Inoue *3–D Natural Interactive Interface Using Marker Tracing from a Single View*, Systems & Computers in Japan, vol. 23, No. 11, 1992, pp. 62–73.

V. Macellari, CoSTEL: "A Computer Peripheral Remote Sensing Device for 3–Dimensional Monitoring of Human Motion", 1983, 21 Med. & Biol. Eng. & Comput. 311.

K. Meyer, et al., "A Survey of Position Trackers", 1992, 1 Presence (No. 2) 173.

J.O.B. Greaves, et al., "A Video–Based Image Analysis System for Rapid Non–Intrusive Data Collection and Reporting of Motion Data", (Citation, if any, unknown). undated.

L. Du, et al., "3–D Grouping by Viewpoint Consistency Ascent", 1991, Britsh Machine Vision Conference 45.

"G.A.W. West, et al., A Survey and Examination of Subpixel Measurement Techniques", 1990, 1395 SPIE 456.

R.L. Andersson, "Real–Time Gray–Scale Video Processing Using a Moment–Generating Chip", 1985, RA–1 IEEE J. of Robotics & Automation (No. 2) 79.

J.C. Trinder, et al., "A Close Range Digital Photogrammetry System", 1990, 1395 SPIE 440.

L.S. Shapiro, et al., "A Modal Approach to Feature–Based Correspondence", 1991, Britsh Machine Vision Conference 78.

A.K.C. Wong, et al., "Constellation Matching: with Application to 3D Object Model Acquistion and Recognition", 1987, Dept. of System Design, U. of Waterloo.

(List continued on next page.)

*Primary Examiner*—David K. Moore
*Assistant Examiner*—Brian P. Werner
*Attorney, Agent, or Firm*—Fish & Richardson P.C.

[57] ABSTRACT

A system for determining the spatial position and angular orientation of an object in real-time is provided having a sensor section and a plurality of activatable markers, adapted for mounting to the object. The plurality of markers are activated simultaneously during each cycle of the sensor section after an initial marker-identification mode and energy emitted by such simultaneously activated markers is detected by the remotely located sensor. With such system, because the markers have been each uniquely identified during the marker-identification mode, and the relative marker geometry is known a prior, the markers can be simultaneously activated, detected and tracked during a subsequent marker-tracking mode. With such an arrangement, less expensive sensors with relatively low sensor cycle rates may be used.

10 Claims, 11 Drawing Sheets

OTHER PUBLICATIONS

Y.C. Kim, et al., "Determining Object Motion in Sequences of Stereo Images", 1987, RA–3 IEEE J. of Robotics & Automation (No. 6) 599.

T.C. Chou, et al., "Recovering 3D Rigid Motions without Correspondence", 1987, IEEE, International Conference on Computer Vision 534.

K. Maurice, et al., "Real–Time Close–Range 3–D Motion Measurements for Dental Medicine", 1990, 1395 SPIE 366.

D. Crouch, "Three Dimensional Reconstruction Using the WATSMART Camera System", 1984, Faculty of Engineering, U. of Waterloo.

D. Geiger, et al., "Stereopsis and Eye–Movement", 1987, IEEE Int'l Conference on Computer Vision 306.

Z. Zang et al., "Motion Analysis of Two Stereo Views and its Applications" (1990) 1395 SPIE 638.

T.N. Tan et al., "Structure from Constrained Motion Using Point Correspondences" (1991) British Machine Conference 301.

P. Morasso et al., "Analysis of Human Movements: Spatial Localisation with Multiple Perspective Views" (1983) 21 Med. & Biol. Eng. & Comput. 74.

K.D. Taylor et al., "An Automated Motion Measurement System for Clinical Gait Analysis" (1982) 15 J. of Biomechanics (No. 7) 505.

W. J. Wilson, "Coordination of Spatial Sensor Information and Image Processing Information" (1986) A.T.C. Defense & Systems Research Division, Honeywell Ltd.

D.A. Simon et al., "Techniques for Fast and Accurate Intrasurgical Registration" (1995) 1 J. of Image Guided Surgery 17.

BrainLAB, "The BrainLAB Neutronavigation System," 1 page, Advertisement, undated.

CoSTEL, "Human Motion Measurement And Analysis," 6 pages, Advertisement, undated.

Motion Analysis Corporation, "The Expertvision™ System," 8 pages, Advertisement, undated.

Northern Digital Inc., "WATSMART A 3–D Motion Analysis System," 4 pages, Advertisement, undated.

Northern Digital Inc., "OPTOTRAK® 3020," 4 pages, Advertisement, undated.

Pixsys, Inc., "Capture the Real World in Real Time . . . , " 4 pages, Advertisement, undated.

Selspot AB, "Human Motion," 12 pages, Advertisement, undated.

Selspot AB, Selspot II, "A Complete System for Sophisticated Motion Analysis," 8 pages, Advertisement, undated.

J.J. Wu, et al., "Recovery of the 3–D Location and Motion of a Rigid Object Through Camera Image", 1988 3 International J. of Computer Vision 373.

| CCD SENSOR CYCLE | m | m+1 | m+2 | m+3 |
|---|---|---|---|---|
| MARKERS 14a-14d | FIRE MARKER 14a ON RIGID BODY 12 | FIRE MARKER 14a AND 14b ON RIGID BODY 12 | FIRE MARKER 14a AND 14c ON RIGID BODY 12 | FIRE MARKER 14a 14c, AND 14d ON RIGID BODY 12 |
| CCD SENSORS 16 left, 16 right | INTEGRATE RAW ENERGY FROM MARKER 14a ON RIGID BODY 12 IN CCD SENSORS 16 left, 16 right | INTEGRATE RAW ENERGY FROM MARKER 14a AND 14b ON RIGID BODY 12 IN CCD SENSORS 16 left, 16 right | INTEGRATE RAW ENERGY FROM MARKER 14a AND 14c ON RIGID BODY 12 IN CCD SENSORS 16 left, 16 right | INTEGRATE RAW ENERGY FROM MARKER 14a, 14c AND 14d ON RIGID BODY 12 IN CCD SENSORS 16 left, 16 right |
| SENSOR PROCESSING CIRCUITRY 17 left, 17 right | SHIFT OUT RAW ENERGY FROM CCD SENSORS 16 left, 16 right, WHICH IS THE RESULT OF FIRING MARKERS 14a-14d, IN CYCLE m-1, PASS THIS ENERGY THROUGH THRESHOLD GATES 33 left, 33 right AND WRITE TO FIFO MEMORIES 34 left, 34 right | SHIFT OUT RAW ENERGY FROM CCD SENSORS 16 left, 16 right, WHICH IS THE RESULT OF FIRING MARKERS 14a, IN CYCLE m, PASS THIS ENERGY THROUGH THRESHOLD GATES 33 left, 33 right AND WRITE TO FIFO MEMORIES 34 left, 34 right | SHIFT OUT RAW ENERGY FROM CCD SENSORS 16 left, 16 right, WHICH IS THE RESULT OF FIRING MARKERS 14a AND 14b IN CYCLE m+1, PASS THIS ENERGY THROUGH THRESHOLD GATES 33 left, 33 right AND WRITE TO FIFO MEMORIES 34 left, 34 right | SHIFT OUT RAW ENERGY FROM CCD SENSORS 16 left, 16 right, WHICH IS THE RESULT OF FIRING MARKERS 14a AND 14c, IN CYCLE m+2, PASS THIS ENERGY THROUGH THRESHOLD GATES 33 left, 33 right AND WRITE TO FIFO MEMORIES 34 left, 34 right |
| FIXED POINT DSPs 20 left, 20 right | CALCULATE CENTROIDS FOR RAW ENERGY WHICH IS THE RESULT OF FIRING MARKER 14a-14d IN CYCLE m-2 | CALCULATE CENTROIDS FOR RAW ENERGY WHICH IS THE RESULT OF FIRING MARKER 14a-14d IN CYCLE m-1 | CALCULATE CENTROIDS FOR RAW ENERGY WHICH IS THE RESULT OF FIRING MARKER 14a IN CYCLE m | CALCULATE CENTROIDS FOR RAW ENERGY WHICH IS THE RESULT OF FIRING MARKER 14a AND 14b IN CYCLE m+1 |

FIG. 4

| CCD SENSOR CYCLE | m | m+1 | m+2 |
|---|---|---|---|
| MARKERS 14a-14d | FIRE MARKERS 14a-14d ON RIGID BODY 12 | FIRE MARKERS 14a-14d ON RIGID BODY 12 | FIRE MARKERS 14a-14d ON RIGID BODY 12 |
| CCD SENSORS 16 left, 16 right | INTEGRATE RAW ENERGY FROM MARKER 14a-14d ON RIGID BODY 12 IN CCD SENSORS 16 left, 16 right | INTEGRATE RAW ENERGY FROM MARKER 14a-14d ON RIGID BODY 12 IN CCD SENSORS 16 left, 16 right | INTEGRATE RAW ENERGY FROM MARKER 14a-14d ON RIGID BODY 12 IN CCD SENSORS 16 left, 16 right |
| SENSOR PROCESSING CIRCUITRY 17 left, 17 right | SHIFT OUT RAW ENERGY FROM CCD SENSORS 16 left, 16 right, WHICH IS THE RESULT OF FIRING MARKERS 14a-14d, IN CYCLE m-1, PASS THIS ENERGY THROUGH THRESHOLD GATES 33 left, 33 right AND WRITE TO FIFO MEMORIES, 34 left, 34 right | SHIFT OUT RAW ENERGY FROM CCD SENSORS 16 left, 16 right, WHICH IS THE RESULT OF FIRING MARKERS 14a-14d, IN CYCLE m, PASS THIS ENERGY THROUGH THRESHOLD GATES 33 left, 33 right AND WRITE TO FIFO MEMORIES, 34 left, 34 right | SHIFT OUT RAW ENERGY FROM CCD SENSORS 16 left, 16 right, WHICH IS THE RESULT OF FIRING MARKERS 14a-14d, IN CYCLE m+1, PASS THIS ENERGY THROUGH THRESHOLD GATES 33 left, 33 right AND WRITE TO FIFO MEMORIES, 34 left, 34 right |
| FIXED POINT DSP's 20 left, 20 right | CALCULATE CENTROIDS FOR RAW ENERGY WHICH IS THE RESULT OF FIRING MARKER 14a-14d IN CYCLE m-2 | CALCULATE CENTROIDS FOR RAW ENERGY WHICH IS THE RESULT OF FIRING MARKER 14a-14d IN CYCLE m-1 | CALCULATE CENTROIDS FOR RAW ENERGY WHICH IS THE RESULT OF FIRING MARKER 14a-14d IN CYCLE m |
| FLOATING POINT DSP 22 | MATCH RAW ENERGY TO MARKERS 14a-14d AND CALCULATE POSE FOR BODY 12 WHICH IS THE RESULT OF FIRING MARKER 14a-14d IN CYCLE m-2 | MATCH RAW ENERGY TO MARKERS 14a-14d AND CALCULATE POSE FOR BODY 12 WHICH IS THE RESULT OF FIRING MARKER 14a-14d IN CYCLE m-1 | MATCH RAW ENERGY TO MARKERS 14a-14d AND CALCULATE POSE FOR BODY 12 WHICH IS THE RESULT OF FIRING MARKER 14a-14d IN CYCLE m |
| HOST COMPUTER 20 DISPLAY 31 | DISPLAY POSE OF BODY 12 WHICH IS THE RESULT OF FIRING MARKER 14a-14d IN CYCLE m-2 | DISPLAY POSE OF BODY 12 WHICH IS THE RESULT OF FIRING MARKER 14a-14d IN CYCLE m-1 | DISPLAY POSE OF BODY 12 WHICH IS THE RESULT OF FIRING MARKER 14a-14d IN CYCLE m |

RIGID BODY 1

| CYCLE | X | Y | Z | YAW | PITCH | ROLL |
|---|---|---|---|---|---|---|
| 33 | 100.5 | -13.5 | -1450.83 | 15.76 | 13.74 | -89.8 |

FIG. 15

RIGID BODY 1

| CYCLE | X | Y | Z | YAW | PITCH | ROLL |
|---|---|---|---|---|---|---|
| 33 | 100.5 | -13.5 | -1450.83 | 15.76 | 13.74 | -89.8 |

RIGID BODY 2

| CYCLE | X | Y | Z | YAW | PITCH | ROLL |
|---|---|---|---|---|---|---|
| 34 | 58.3 | 74.9 | -2450.98 | -13.83 | 0.87 | 75.98 |

| CCD SENSOR CYCLE | m | m+1 | m+2 |
|---|---|---|---|
| MARKERS 14a-14d | FIRE MARKERS 14a-14d ON RIGID BODY 12a | FIRE MARKERS 14a-14d ON RIGID BODY 12b | FIRE MARKERS 14a-14d ON RIGID BODY 12a |
| CCD SENSORS 16 left, 16 right | INTEGRATE RAW ENERGY FROM MARKER 14a-14d ON RIGID BODY 12a IN CCD SENSORS 16 left, 16 right | INTEGRATE RAW ENERGY FROM MARKER 14a-14d ON RIGID BODY 12b IN CCD SENSORS 16 left, 16 right | INTEGRATE RAW ENERGY FROM MARKER 14a-14d ON RIGID BODY 12a IN CCD SENSORS 16 left, 16 right |
| SENSOR PROCESSING CIRCUITRY 17 left, 17 right | SHIFT OUT RAW ENERGY FROM CCD SENSORS 16 left, 16 right, WHICH IS THE RESULT OF FIRING MARKERS 14a-14d, ON BODY 12b IN CYCLE m-1, PASS THIS ENERGY THROUGH THRESHOLD GATES 33 left, 33 right AND WRITE TO FIFO MEMORIES, 34 left, 34 right | SHIFT OUT RAW ENERGY FROM CCD SENSORS 16 left, 16 right, WHICH IS THE RESULT OF FIRING MARKERS 14a-14d, ON BODY 12a IN CYCLE m, PASS THIS ENERGY THROUGH THRESHOLD GATES 33left, 33 right AND WRITE TO FIFO MEMORIES, 34 left, 34 right | SHIFT OUT RAW ENERGY FROM CCD SENSORS 16 left, 16 right, WHICH IS THE RESULT OF FIRING MARKERS 14a-14d, ON BODY 12b IN CYCLE m+1, PASS THIS ENERGY THROUGH THRESHOLD GATES 33 left, 33 right AND WRITE TO FIFO MEMORIES, 34 left, 34 right |
| FIXED POINT DSP's 20 left, 20 right | CALCULATE CENTROIDS FOR RAW ENERGY WHICH IS THE RESULT OF FIRING MARKER 14a-14d ON BODY 12a IN CYCLE m-2 | CALCULATE CENTROIDS FOR RAW ENERGY WHICH IS THE RESULT OF FIRING MARKER 14a-14d ON BODY 12b IN CYCLE m-1 | CALCULATE CENTROIDS FOR RAW ENERGY WHICH IS THE RESULT OF FIRING MARKER 14a-14d ON BODY 12a IN CYCLE m |
| FLOATING POINT DSP 22 | MATCH RAW ENERGY TO MARKERS 14a-14d AND CALCULATE POSE FOR BODY 12 WHICH IS THE RESULT OF FIRING MARKER 14a-14d IN CYCLE m-2 | MATCH RAW ENERGY TO MARKERS 14a-14d AND CALCULATE POSE FOR BODY 12 WHICH IS THE RESULT OF FIRING MARKER 14a-14d ON BODY 12b IN CYCLE m-1 | MATCH RAW ENERGY TO MARKERS 14a-14d AND CALCULATE POSE FOR BODY 12a WHICH IS THE RESULT OF FIRING MARKER 14a-14d ON BODY 12a IN CYCLE m |
| HOST COMPUTER 20 DISPLAY 31 | DISPLAY POSE OF BODY 12a WHICH IS THE RESULT OF FIRING MARKER 14a-14d IN CYCLE m-2 | DISPLAY POSE OF BODY 12b WHICH IS THE RESULT OF FIRING MARKER 14a-14d IN CYCLE m-1 | DISPLAY POSE OF BODY 12a WHICH IS THE RESULT OF FIRING MARKER 14a-14d IN CYCLE m |

FIG. 14

SYSTEM FOR DETERMINING THE SPATIAL POSITION AND ANGULAR ORIENTATION OF AN OBJECT

BACKGROUND OF THE INVENTION

This invention relates generally to systems for determining the spatial position and angular orientation of an object and more particularly to systems of such type wherein the object emits energy from points on the object.

As is known in the art, systems are available for determining the spatial position and angular orientation of an object. One such system includes passive retro-reflectors as markers affixed to the object and a second system includes active radiating emitters as the affixed markers. Both techniques operate by projecting the image of a high contrasting marker onto spaced sensors and using mathematical processing to determine the three dimensional coordinates of each one of the markers. These three dimensional coordinates (i.e., 3D) are then used as discrete points, or may be considered as a set if their geometric arrangement is known, resulting in the determination of the position and angular orientation of the object (i.e., six degrees of freedom: x,y and z positions and pitch, yaw and roll angular orientations) in space relative to a three dimensional coordinate system centered at a preselected point in space, typically at a point fixed relative to the sensors. Thus, the object may be used in many applications, for example as a digitizing pointer held by hand as in reverse engineering applications or to measure human motion and performance. For example, the object may be mounted to different points on the leg of an athlete, such as a track runner. While the runner is exercising, as for example on a treadmill, the system enables detailed observation of various parts of the runner's legs and, from such observation, modification of the runner's running style may be suggested.

In one active radiating emitter system, multiple charge coupled device (CCD) sensors are used to detect the energy radiated by the marker. A single marker is energized per sensor cycle to emit infrared energy. During each sensor cycle, the emitted energy focussed onto the sensor is collected (i.e., integrated) and shifted to sensor processing circuitry. In order to determine the 6D position and angular orientation of the object, at least three points on the object must be detected by a sufficient number of the sensors (i.e. to cover a minimum of 3 orthogonal planes). Thus, to account for the possibility that one of the markers may be obscured from the sensors, the object typically has affixed to it at least four, but generally six to twenty-four, markers. Thus, where the object has four markers, four sensor cycles are used to produce a frame of data. Further, in order to keep track of each one of the markers, each marker is activated in a known, corresponding one of the four cycles during each frame, i.e., cycle 1 for marker 1, cycle 2 for marker 2, etc. While this approach is very robust because each marker is readily identifiable (i.e., only one marker is activated per sensor cycle), such system requires the use of high speed, relatively expensive sensors in order to track an object moving at a relatively high speed. For example, in order to track the motion of the lower arm, which could have a frequency of motion as high as 30 Hz, sampling rates of 60 Hz may be required. In this system the sampling rate is equivalent to the sensor cycle rate divided by the number of markers. With the four sequentially activated marker system, however, each one of the four markers must be activated at 60 Hz and the CCD sensor must be activated at 240 Hz. CCD sensors which operate at such high cycle rates are relatively expensive.

SUMMARY OF THE INVENTION

In accordance with the present invention, a system for determining the spatial position and angular orientation of an object is provided having a sensor section and a plurality of activatable markers adapted for mounting to the object. The object is a rigid body and the markers are affixed to the rigid body in a known, fixed relationship to each other and to the geometry of the body. After an initial marker-identification mode, the plurality of markers are activated simultaneously during each sensor cycle and energy emitted by such simultaneously activated markers is detected and tracked during a subsequent marker-tracking mode. With such system, because the markers have been each uniquely identified during the marker-identification mode, the markers can be simultaneously activated, detected and tracked in real-time during the subsequent marker-tracking mode. With such arrangement, less expensive sensors with relatively low sensor cycle rates may be used.

In a preferred embodiment of the invention, the system includes: a plurality of activatable markers, preferably infrared emitting markers, affixable to an object; a sensor section, preferably a pair of infrared two-dimensional array, CCD sensors, for providing signals representative of positional information of energy emitted by at least one of the markers on to the sensors; a processing section, preferably including a pair of fixed point digital signal processors (DSPs) responsive to the signals produced by the sensor section, for determining the position of a marker's emitted energy at the sensor and a floating point DSP for matching the markers with the positional information to identify the position of each marker relative to the sensor and from such matching determining the orientation of the object from the position determined by the pair of fixed point DSPs; and, a marker sequencer and controller for controlling the activation of the emitters during the marker-identification and marker-tracking modes in response to information produced by the floating point DSP. This marker sequencer and controller sequentially activates the markers at appropriate times during the marker-identification mode, and simultaneously activates the markers during the marker-tracking mode. The floating point DSP generates the object spatial orientation (i.e., six degrees of freedom, 6D orientation of the object: x, y, z linear position and pitch, yaw and roll angular orientation) and communicates such information to a host computer. The host computer displays such information.

BRIEF DESCRIPTION OF THE DRAWINGS

Other features of the invention will become more readily apparent with reference to the following description taken together with the following drawings, in which:

FIG. 4 is a diagram showing the activity of various components of the system of FIG. 1 during a sequence of sensor cycles performed during an initial marker-identification mode;

FIG. 11 is a diagram showing the activity of various components of the system of FIG. 1 during a sequence of sensor cycles performed during the marker-tracking mode;

FIG. 12 is a table presented on a display of the system of FIG. 1 of data representing a pose of the rigid body;

FIG. 14 is a diagram showing the activity of various components of the system of FIG. 13 during a sequence of sensor cycles performed during the marker-tracking mode; and FIG. 15 is a table presented on a display of the system of FIG. 13 of data representing a pose of each of the rigid objects.

DESCRIPTION OF THE PREFERRED EMBODIMENTS

Figure 1:
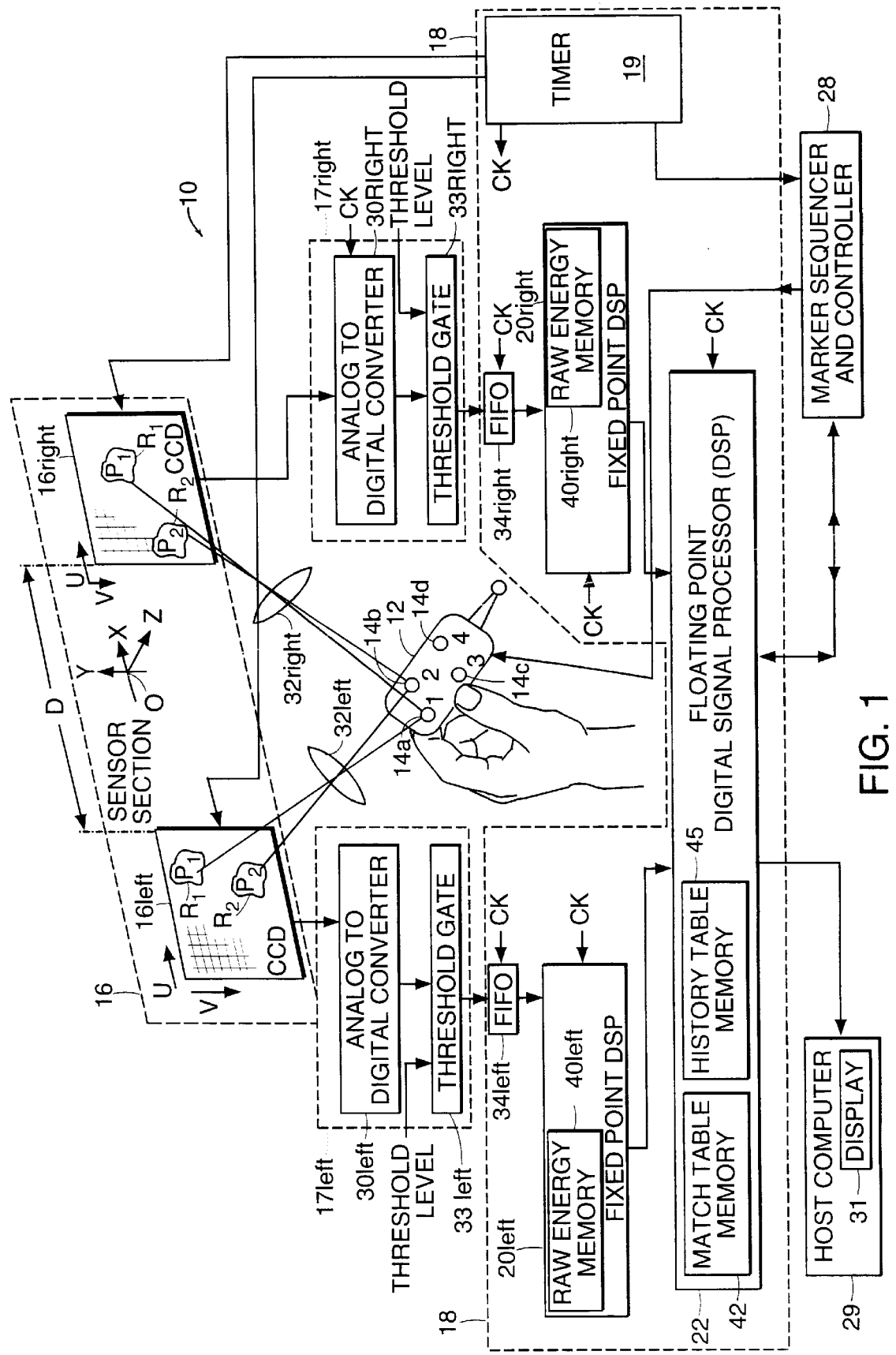
FIG. 1 is a block diagram of a system for determining the spatial position and orientation of a rigid body according to the invention.

Referring now to FIG. 1, a system 10 for determining the spatial position and orientation of a rigid object 12 is provided wherein a plurality of, here four, active emitters or markers 14a, 14b, 14c and 14d, affixed to the object 12 are activated simultaneously after an initial marker-identification mode and energy emitted by such markers 14a–14d is detected by a remotely located sensor section 16. Here, the sensor section 16 includes a pair of spaced sensors $16_{left}$, $16_{right}$. More particularly, system 10 determines the positions of at least three of the four markers 14a–14d in common for both sensors $16_{left}$, $16_{right}$ and from such determined positions, determines the spatial position and angular orientation of the object 12 (i.e., six degrees of freedom: x, y, and z positions and pitch, yaw and roll angular orientations) in space relative to a three dimensional coordinate system centered at a preselected point, O, in space, here centered at a point mid-way between the sensors $16_{left}$, $16_{right}$. Thus, as shown in FIG. 1, the x-axis is a horizontal axis, the y-axis is a vertical axis, and the z-axis is an axis perpendicular to the x-y plane. With such system 10, because the markers 14a–14d have been each uniquely identified during the marker-identification mode in a manner to be described, the markers 14a–14d can be simultaneously activated, detected and tracked during a subsequent marker-tracking mode.

More particularly, the system 10 includes as the plurality of, here four, active markers 14a–14d, infrared energy emitting markers. The pair of sensors $16_{left}$, $16_{right}$, here two two-dimensional array CCD sensors, each adapted to produce output signals which represent the intensity of energy focussed thereon. During each sensor cycle, the emitted energy focussed to the sensors $16_{left}$, $16_{right}$ is collected (i.e., integrated) and shifted to sensor processing circuitry $17_{left}$, $17_{right}$. Here, the sensors $16_{left}$, $16_{right}$ are mounted to a fixed reference and are separated from each other by a predetermined distance, D, here 500 mm. Here, the sensors $6_{left}$, $16_{right}$ have a field of view sufficient to observe a common measurement volume of a 1 meter sphere centered at approximately 1.9 meters from the sensors $16_{left}$, $16_{right}$ along the z-axis.

The processing section 18 including a timer 19 and a pair of fixed point digital signal processors (DSPs) $20_{left}$, $20_{right}$ coupled to a corresponding one of the pair of sensors $16_{left}$, $16_{right}$ through a corresponding one of the pair of sensor processing circuitry $17_{left}$, $17_{right}$ for determining the two dimensional u, v positions of energy emitted by the activated markers 14a–14d and focused onto the sensors $16_{left}$, $16_{right}$. The timer 19 produces clock pulses CK at the sensor $16_{left}$, $16_{right}$ cycle rates. The processing section 18 includes a floating point DSP 22 for first matching the determined focused energy positions on the sensors $16_{left}$, $16_{right}$ with the markers 14a–14d. Then, from the determined positions of at least three of the markers 14a–14d in common for both sensors $16_{left}$, $16_{right}$, relative to the sensors $16_{left}$, $16_{right}$, the floating point DSP 22 determines the 6D spatial orientation of the object (i.e., the 6D orientation reference to the x, y, z coordinate system centered at point, 0, and discussed above).

A marker sequencer and controller 28, is provided for controlling the activation of the markers 14a–14d during the marker-identification and marker-tracking modes in response to information produced by the floating point DSP 22. More particularly, the marker sequencer and controller 28 sequentially activates the markers 14a–14d at appropriate times during the marker-identification mode, and marker-tracking mode.

The floating point DSP 22 generates the object spatial orientation (i.e., six degrees of freedom, 6D orientation of the object: x, y, z linear position and pitch, yaw and roll angular orientation) and communicates such information to a host computer 29. The host computer 29 displays such information in display 31.

MARKER-IDENTIFICATION MODE

Figure 2:
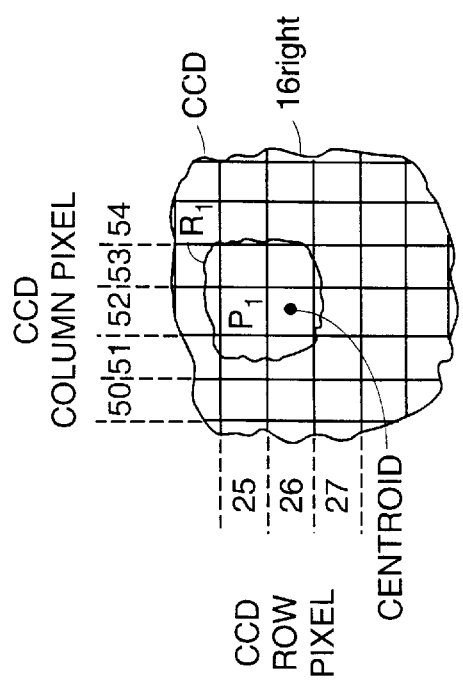
FIG. 2 is a diagram showing energy emitted by a marker used in the system of FIG. 1 focussed to a point on a sensor of the system of FIG. 1.

Briefly, during the marker-identification mode, the markers 14a–14d are pulsed with current from the marker sequencer and controller 28 and in response to such pulsed current emit light, here infrared energy. This emitted energy is transmitted through lenses $32_{left}$, $32_{right}$ and focused onto the two-dimensional array CCD sensors $16_{left}$, $16_{right}$, respectively. Each one of the sensors $16_{left}$, $16_{right}$ has, as noted above, an mxn array of m-rows and n-columns of pixels, where a pixel is analogous to a bucket which collects the energy focused on it. The rows of pixels are along the u-direction and the columns of pixels are along the v-direction, as shown in FIG. 1. Thus, as shown in FIG. 1, the energy emitted by marker 14a, for example, is focused to region $R_1$ and the energy from marker 14b is focussed to region $R_2$ of the sensors $16_{left}$, $16_{right}$, by lenses $32_{left}$, $32_{right}$, respectively as shown. Thus, considering for example sensor $16_{left}$, as shown in FIG. 2, here the center of mass of the energy (i.e., the centroid of the energy) in region $R_1$ is at a point $P_1$ located at u,v coordinates u=52.875, v=26.173. That is, the centroid of the energy is determined to sub-pixel accuracy.

Figure 3:
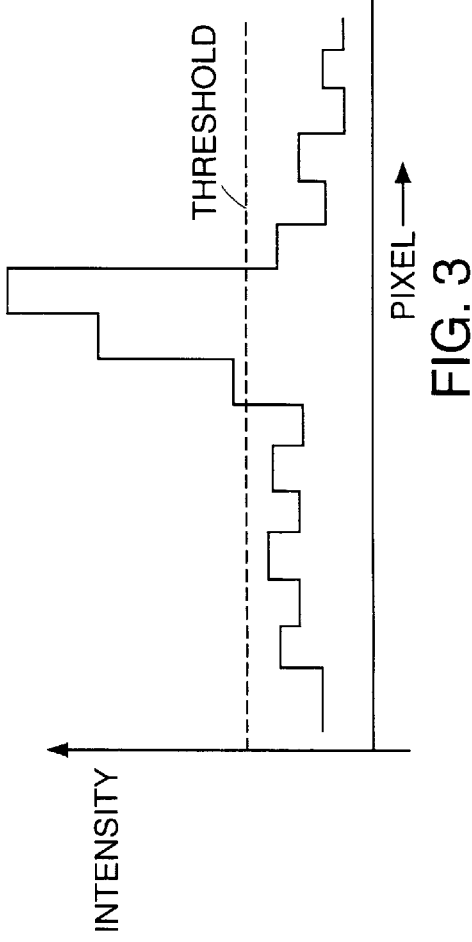
FIG. 3 is a time history of energy collected by a row of pixels on the sensor of FIG. 2 as such energy is shifted from the sensor to sensor processing circuitry of the system of FIG. 1.

More particularly, during each cycle of the CCD sensors $16_{left}$, $16_{right}$ the energy in the pixels is shifted out of the CCD one row at a time into the sensor processing circuitry $17_{left}$, $17_{right}$, respectively, in a conventional manner. The energy (i.e, corresponding voltage) is converted into digital data by analog to digital converters $30_{left}$, $30_{right}$. Energy greater than a predetermined threshold passes through threshold gates $33_{left}$, $33_{right}$ for storage in first in-first out (FIFO) memories $34_{left}$, $34_{right}$, respectively. Referring to FIG. 3, an example of the relationship between intensity detected by one of the sensors $16_{left}$, $16_{right}$ and a row of pixels thereof is shown together with the predetermined threshold level. The intensity level for pixels having intensity levels greater than the threshold level will be stored in the FIFO memories $34_{left}$, $34_{right}$. Thus, thresholding is performed to decrease the amount of data to be stored and processed. After the last pixel has been loaded into the FIFO memories $34_{left}$, $34_{right}$, the fixed point DSPs $20_{left}$, $20_{right}$ perform the above described centroid calculation. This is a pipeline process summarized in FIG. 4.

A marker-identification mode is required because the "raw energy" retrieved (as shown in FIG. 3 ) from the CCD sensors $16_{left}$, $16_{right}$ is not directly identified with the markers but, rather, is retrieved as energy at a pixel, or sub-pixel, position on the sensors $16_{left}$, $16_{right}$. The correspondence between the "raw energy" retrieved from the sensors $16_{left}$, $16_{right}$ and the particular marker on the rigid body producing such "raw" energy is therefore not directly known from the data retrieved directly from the sensors $16_{left}$, $16_{right}$. Thus, a marker-identification mode is required. The marker-identification mode, to be described, will form the correspondence between the "raw energy" data retrieved directly from the sensors $16_{left}$, $16_{right}$ and the particular marker that emitted such "raw energy" data.

During the marker-identification mode, the u, v position of the focussed energy on the sensors $16_{1eft}$, $16_{right}$ is determined by the fixed point DSPs $20_{left}$, $20_{right}$ and stored in RAW ENERGY memories $40_{left}$, $40_{right}$. It is noted that the u, v position (i.e. memory location) in the RAW ENERGY memories $40_{left}$, $40_{right}$ will correspond to the sequence in which the focussed energy (i.e., the centroid of the energy) is detected and shifted out of the CCD sensors $16_{left}$, $16_{right}$. This memory location therefore, may be different from the one of the markers 14a–14d producing the focussed energy. To put it another way, the two RAW ENERGY memories $40_{left}$, $40_{right}$ provide two tables which provide the location of the energy detected on the CCD sensors $16_{left}$, $16_{right}$ from the activated one, or ones of the markers 14a–14d. The order in these RAW ENERGY memories $40_{left}$, $40_{right}$ is seldom relative to the true marker number (i.e., assuming markers 14a–14d are markers 1–4, respectively) and is generated in the sequence in which the energy is retrieved, i.e., shifted from the CCD sensors $16_{left}$, $16_{right}$. Here the u, v position is a pixel/sub-pixel position, as discussed above in connection with FIG. 2.

More particularly, assume for example that the rigid body is a hand held pointing device as shown in FIG. 1. Further, here the pointing device has affixed to it four markers 14a–14d, as shown. First the marker-identification mode is used during which a single marker, here marker 14a is activated during a first CCD cycle (i.e., cycle 1). In this example, sensor $16_{left}$ indicates energy at u=50, v=50 and sensor $16_{right}$ indicates energy at u=75, v=50.5. Thus, the RAW ENERGY memories $40_{left}$, $40_{right}$ stored data as follows:

| MEMORY LOCATION | u position | v position |
| --- | --- | --- |
| RAW ENERGY MEMORY $40_{left}$ | | |
| 1 | 50 | 50 |
| RAW ENERGY MEMORY $40_{right}$ | | |
| 1 | 75 | 50.5 |

Because only one marker, i.e., marker 14a is activated during cycle 1, the detected energy must be from marker 14a. Thus, the position of marker 14a relative to sensors $16_{left}$, $16_{right}$, is known.

Next, both markers 14a and 14b are activated during a second CCD cycle (i.e., cycle 2). Assume in this example that marker 14b is blocked from sensors $16_{left}$, $16_{right}$. Thus, during cycle 2, sensor $16_{left}$ indicates energy at position u=50.25, v=50.3 and the right sensor $16_{right}$ indicates energy at u=75.25, v=50.8. Thus, the RAW ENERGY memories $40_{left}$, $40_{right}$ stored data as follows:

| MEMORY LOCATION | u position | v position |
| --- | --- | --- |
| RAW ENERGY MEMORY $40_{left}$ | | |
| 1 | 50.25 | 50.3 |
| RAW ENERGY MEMORY $40_{right}$ | | |
| 1 | 75.25 | 50.8 |

Figure 5:
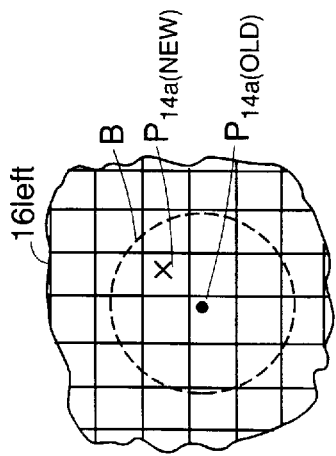
FIGS. 5 through 9 are diagrams of markers being tracked by the system of FIG. 1 at various steps in the operation of such system, such diagrams useful in understanding the operation of the system of FIG. 1, FIGS. 5–7 showing a position of a marker or markers during the initial marker identification mode and FIGS. 8 and 9 showing markers during a marker tracking mode.

From the position of marker 14a l *determined in cycle* 1, the floating point DSP 22 examines whether there is detected energy within a predetermined circular boundary, B, here a radius of 2 pixels, of the previous, cycle 1 position of the marker 14a, as shown in FIG. 5. Here, in this example, because there is only one marker 14a in the circular boundary, B, the floating point DSP 22 concludes that it is identifying only marker 14a and that the floating point DSP 22 is unable to find the marker 14b. (It is noted in FIG. 5 that the position of marker 14a on sensor $16_{left}$ during cycle 1 is indicated by point $P_{14a(old)}$ and the position of marker 14a on sensor $16_{left}$ during cycle 2 is indicated by point $P_{14a\,(new)}$).

Figure 6:
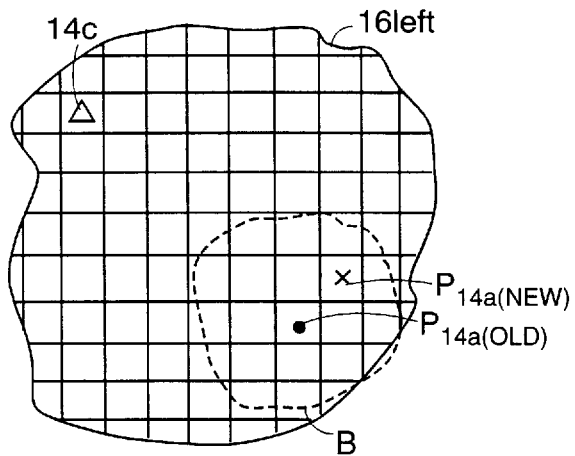

During cycle 3, markers 14a and 14c are activated. As noted above, the previous position of marker 14a, i.e., the positions of marker 14a during cycle 2 relative to the sensors $16_{left}$, $16_{right}$ were u=50.25, v=50.3 and u=75.25, v=50.8, respectively. Here, during cycle 3, energy is detected at the following two positions: For sensor $16_{left}$, u=25, v=80 and u=50.5, v=50.6; and for sensor $16_{right}$, u=75.5, v=51.1 and u=50, v=80, as shown in FIG. 6. Thus, the data in the RAW ENERGY memories $40_{left}$, $40_{right}$ is as follows:

| MEMORY LOCATION | u position | v position |
| --- | --- | --- |
| RAW ENERGY MEMORY $40_{left}$ | | |
| 1 | 25 | 80 |
| 2 | 50.50 | 50.6 |
| RAW ENERGY MEMORY $40_{right}$ | | |
| 1 | 75.25 | 51.1 |
| 2 | 50 | 80 |

From the position of marker 14a in cycle 2, the floating point DSP 22 examines whether there is detected energy within the predetermined circular boundary, B, (FIG. 6) of the previous, cycle 2 position of the marker 14a. Here, in this example, there is energy at u=50.50, v=50.6 (for sensor $16_{left}$) and u=75.5, v=51.1 (for sensor $16_{right}$); i.e., a position within the predetermined circular boundary, B, for marker 14a. Further, there is energy outside the boundary, B; i.e., at u=25, v=80 (for sensor $16_{left}$) and u=50, v=80 (for sensor $16_{right}$). The floating point DSP 22 thus matches the marker 14c with the energy at u=25, v=80 (for sensor $16_{left}$) and u=50, v=80 (for sensor $16_{right}$) and stores the following information into match-memory 42, as follows:

| MARKER NUMBER | u position | v position |
|---|---|---|
| MATCH-MEMORY 42 (FOR SENSOR $16_{left}$) | | |
| 14a | 50.50 | 50.6 |
| 14b | MISSING | MISSING |
| 14c | 25 | 80 |
| 14d | MISSING | MISSING |
| MATCH-MEMORY 42 (FOR SENSOR $16_{right}$) | | |
| 14a | 75.5 | 51.1 |
| 14b | MISSING | MISSING |
| 14c | 50 | 80 |
| 14d | MISSING | MISSING |

Thus, a match memory table exists within the match-memory 42 of the floating point DSP 22 and represents the true 2D position of the rigid body markers 14a–14d for both sensors 14$_{left}$, 14$_{right}$. There is one row in the match memory table for each one of the markers 14a–14d on the body 12. The RAW ENERGY locations are thus sorted and matched to the true marker 14a–14d locations. If one of the markers 14a–14d is out of view or not matched the location is set to "MISSING" as shown in the example above. The 2D locations are given in u, v coordinates where, as noted above, u is the horizontal pixel position along the CCDs and v is the vertical pixel position.

Figure 7:
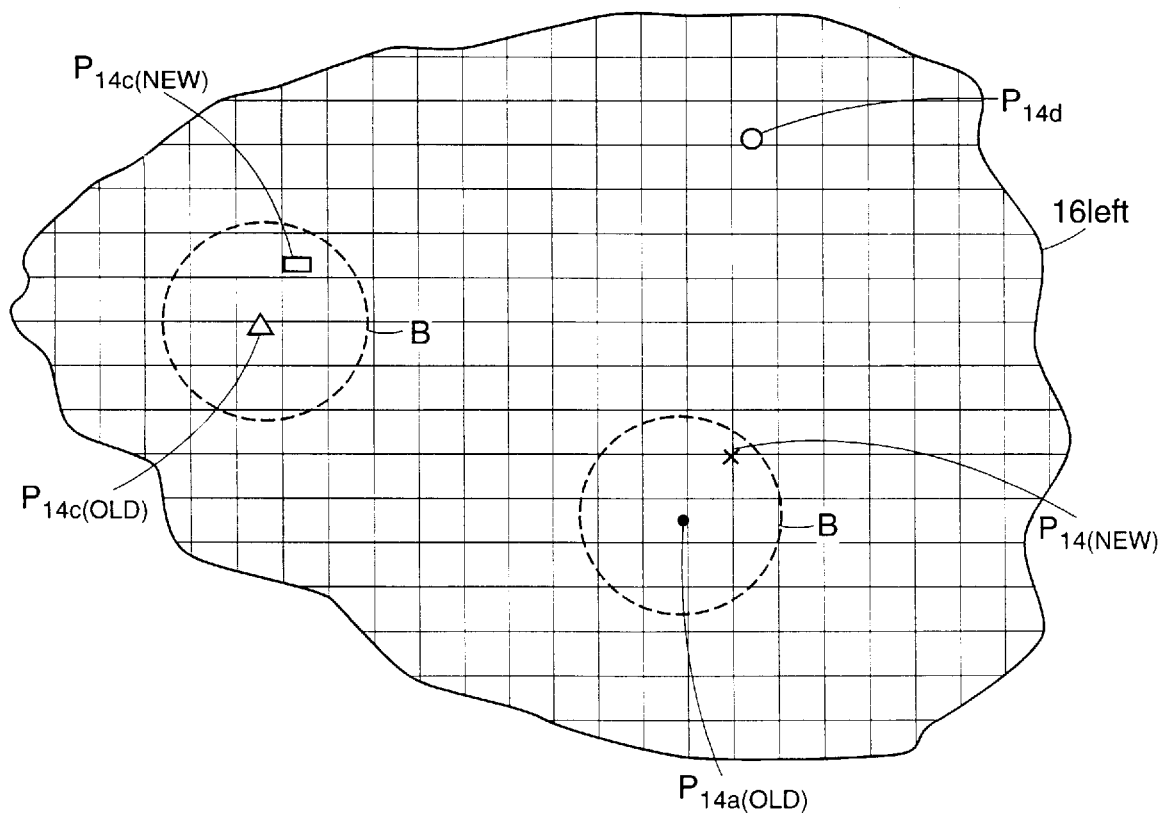

Next, during the next CCD cycle (i.e. cycle 4), markers 14a, 14c and 14d are activated. Energy is detected at the following points (FIG. 7) and therefore the data in the RAW ENERGY memories 40$_{left}$, 40$_{right}$ is as follows:

| MEMORY LOCATION | u position | v position |
|---|---|---|
| RAW ENERGY MEMORY $40_{left}$ | | |
| 1 | 100 | 120 |
| 2 | 25.3 | 80.3 |
| 3 | 50.75 | 50.9 |
| RAW ENERGY MEMORY $40_{right}$ | | |
| 1 | 125 | 120 |
| 2 | 75.75 | 51.4 |
| 3 | 50.25 | 80.3 |

Thus, the DSPs provides the following matching data into the match-memories:

| MARKER NUMBER | u position | v position |
|---|---|---|
| MATCH-MEMORY 42 (FOR SENSOR $16_{left}$) | | |
| 14a | 50.75 | 50.9 |
| 14b | MISSING | MISSING |
| 14c | 25.3 | 80.3 |
| 14d | 100 | 120 |
| MATCH-MEMORY 42 (FOR SENSOR $16_{right}$) | | |
| 14a | 75.75 | 51.4 |
| 14b | MISSING | MISSING |
| 14c | 50.25 | 80.3 |
| 14c | 125 | 120 |

The floating point DSP now has sufficient data, i.e., data from 3 points on the rigid body in common for each of the pair of sensors to determine the spatial, 6D, orientation of the rigid body 12.

During cycle 5, markers 14a, 14c and 14d are activated simultaneously as in cycle 4 and assume the match-memories 42 identification remains unchanged because the same markers 14a, 14c, 14d are still visible and their movement does not exceed the specified boundary.

MARKER-TRACKING MODE

Figure 8:
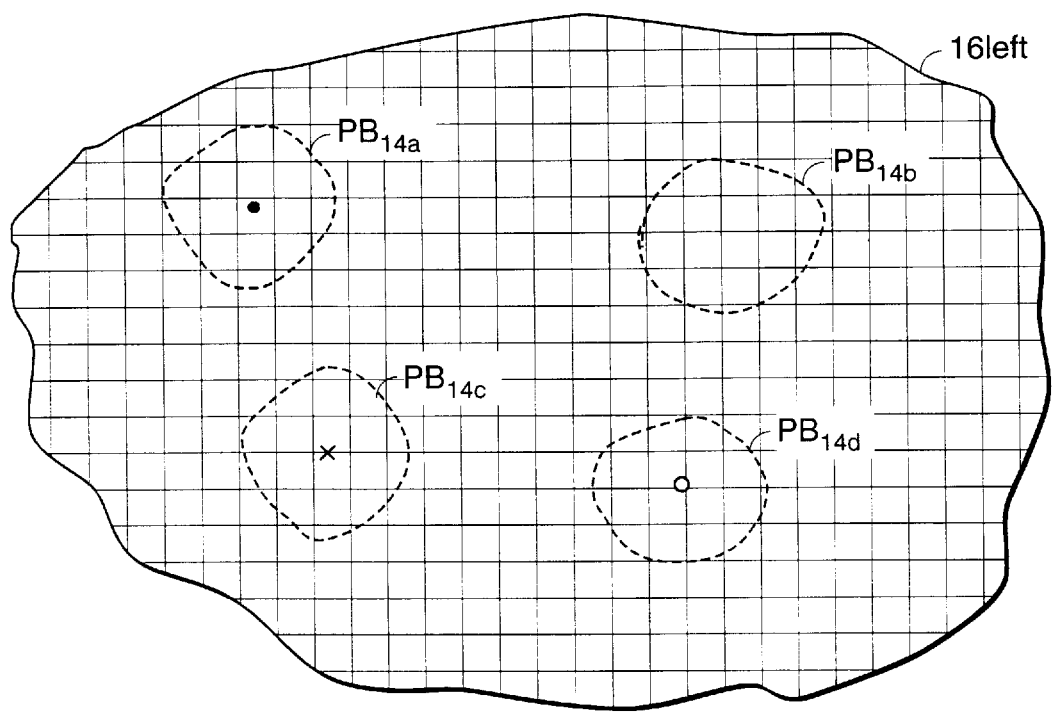

During the sixth cycle of the CCD (i.e., cycle 6) the following steps are performed by the floating point DSP 22:

(Step 6-1) All markers 14a–14d are simultaneously activated by the marker sequencer and controller 28;

(Step 6-2) A six degrees of freedom prediction calculation is made to generate an extrapolated six degrees of freedom position and angular orientation;

(Step 6-3) The estimate of the new position is then mathematically projected onto the two sensors 16$_{left}$, 16$_{right}$ u, v coordinate system to generate two dimensional coordinates for each marker on the object;

(Step 6-4) The estimated position is matched against the actual u,v coordinates collected by placing an associated mathematical window, i.e., circular predicted boundary, PB, around each estimate, as shown in FIG. 8. A "nearest neighbor" algorithm is applied to the u,v coordinates to associate them with the calculated estimates, by means of this prediction boundary. Thus, predicted boundary windows $PB_{14a}$–$PB_{14d}$ are placed around the positions of the markers 14a–14d, respectively. It should be noted that while marker 14b is here assumed to be obscured, the floating point DSP 22 is able to predict its position because of the known relationship among the markers 14a–14d.

(Step 6-5) With at least three markers 14a–14d in common identified by both sensors 16$_{left}$, 16$_{right}$ a six degrees of freedom position of the rigid body 12 may be calculated.

(Step 6-6) When one of the markers 14a–14d is obscured, it is possible to extrapolate the position so that it may once again be tracked when it comes back into view. This is possible because the system has a prior knowledge of the spatial relationship among the markers 14a–14d and their fixed relationship to the geometry c)f the rigid body 12.

(Step 6-7) Loop through Steps 6-1through 6-6 until less than three common markers 14a-14d for both the left and right sensors 16$_{left}$, 16$_{right}$ are identified. In such case, the process jumps back to the marker-identification mode.

More particularly, a history table is stored in a HISTORY TABLE memory 45 of the floating point DSP 22. The data in the history table represents the true (i.e. coordinate x, y, z system) 6D position and angular orientation of the rigid body 12. There is one row in the history table for each past M 6D determined positions. Here, M is an integer greater than or equal to 2. The greater the value of M the better the prediction will be of the next cycle's rigid body 6D position. An example of a history table is shown below where the x, y, and z position of the body is here expressed in millimeters (mm) and the yaw, pitch, and roll angular orientations are expressed in degrees, where the current sensor cycle is N:

| HISTORY TABLE | | | | | | |
|---|---|---|---|---|---|---|
| Cycle # | x | y | z | yaw | pitch | roll |
| N-1 | 100 | 50 | −1500 | 45 | 0 | 87 |
| N-2 | 101 | 52 | −1503 | 46 | 1 | 86 |
| N-3 | 102 | 54 | −1506 | 44 | 1.5 | 85 |

Figure 9:
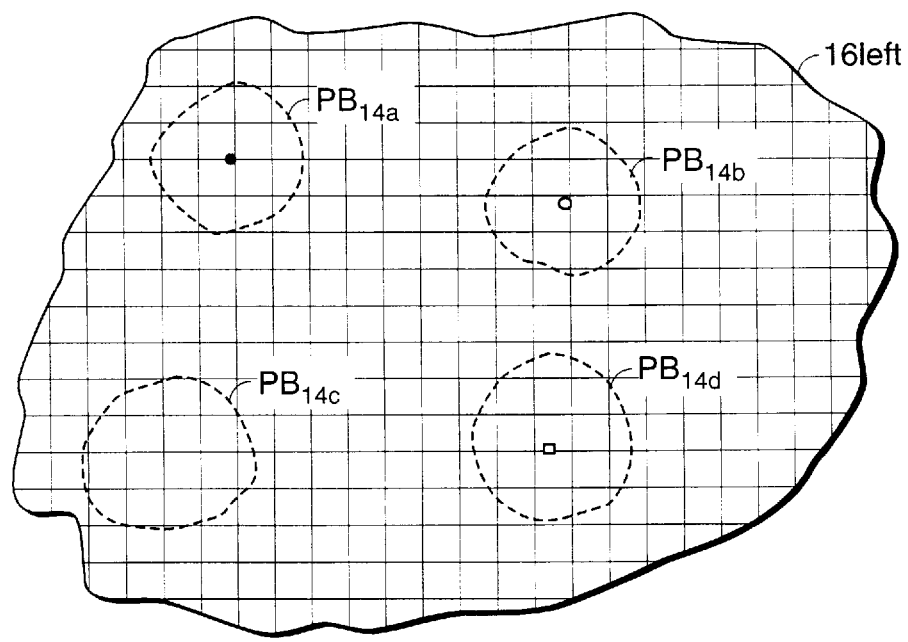

During the seventh CCD cycle (i.e., cycle 7), let it be assumed that marker 14c drops out of view and marker 14b appears, as shown in FIG. 9. Here steps 6-1 through 6-4 repeat from cycle 6. The floating point DSP 22 tracks markers 14a, 14b and 14d; noting that marker 14c is missing. Because at least three marker positions in common are known, u, v positional data is matched in match-memory 42 for markers 14a, 14b and 14d and 3D and then 6D position and angular orientation of object 12 may be calculated.

During the eighth CCD cycle (i.e., cycle 8), steps 6-1 through 6-4 for cycle 6 are repeated until less than the minimum number of markers 14a–14d (i.e., less than 3) are visible on both the sensors $16_{left}$ and $16_{right}$. In the event that the minimum number of markers 14a–14d are not visible on both the sensors $16_{left}$ and $16_{right}$, the marker-identification mode, discussed above, is re-instituted.

Figure 10A:
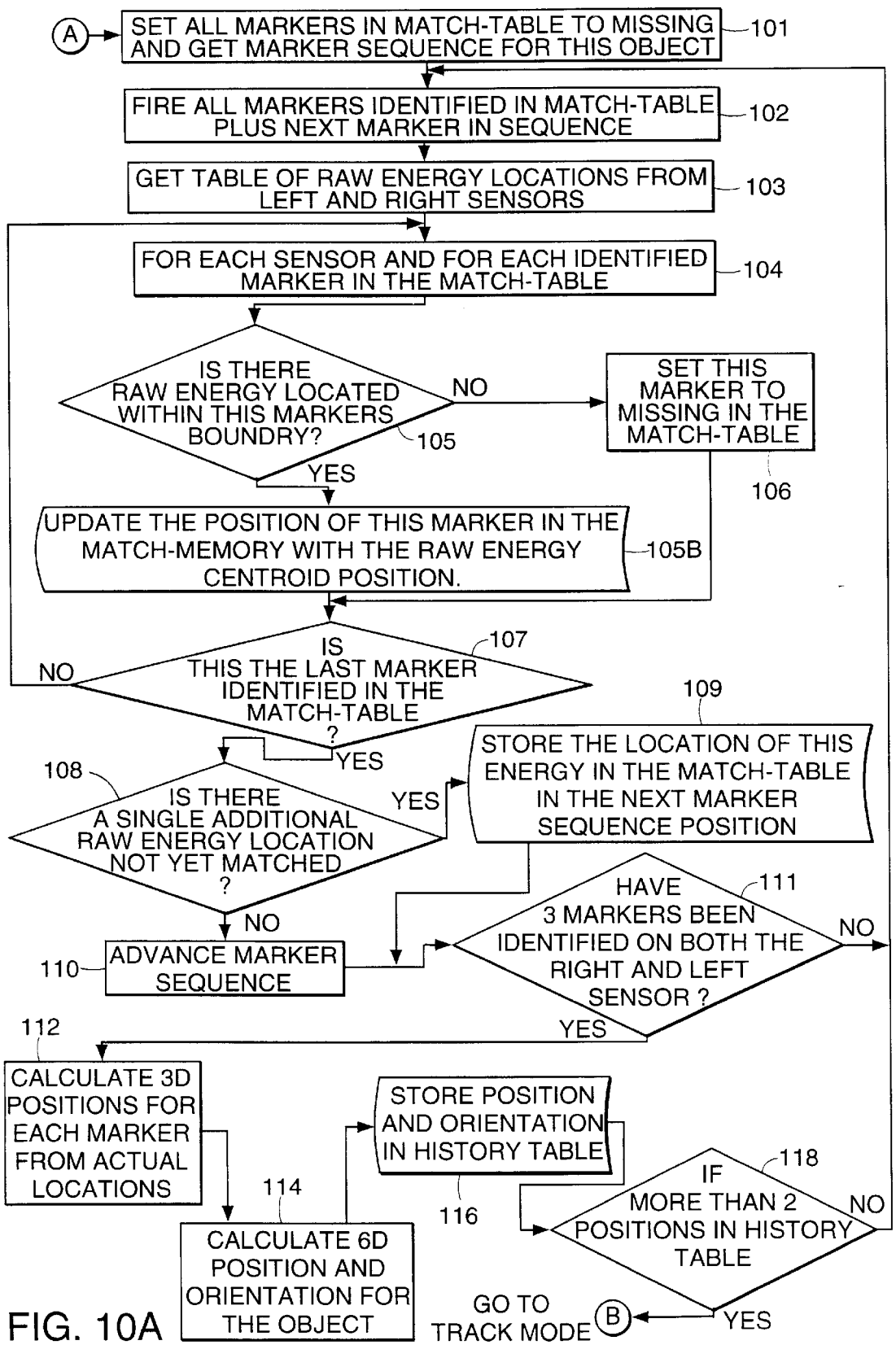
FIGS. 10A and 10B are flow diagrams of the process used by the system of FIG. 1 in determining the spatial position and orientation of the rigid body, FIG. 10A being a flow diagram for the initial marker-identification mode and FIG. 10B being a flow diagram for a subsequent marker-tracking mode.
Figure 10B:
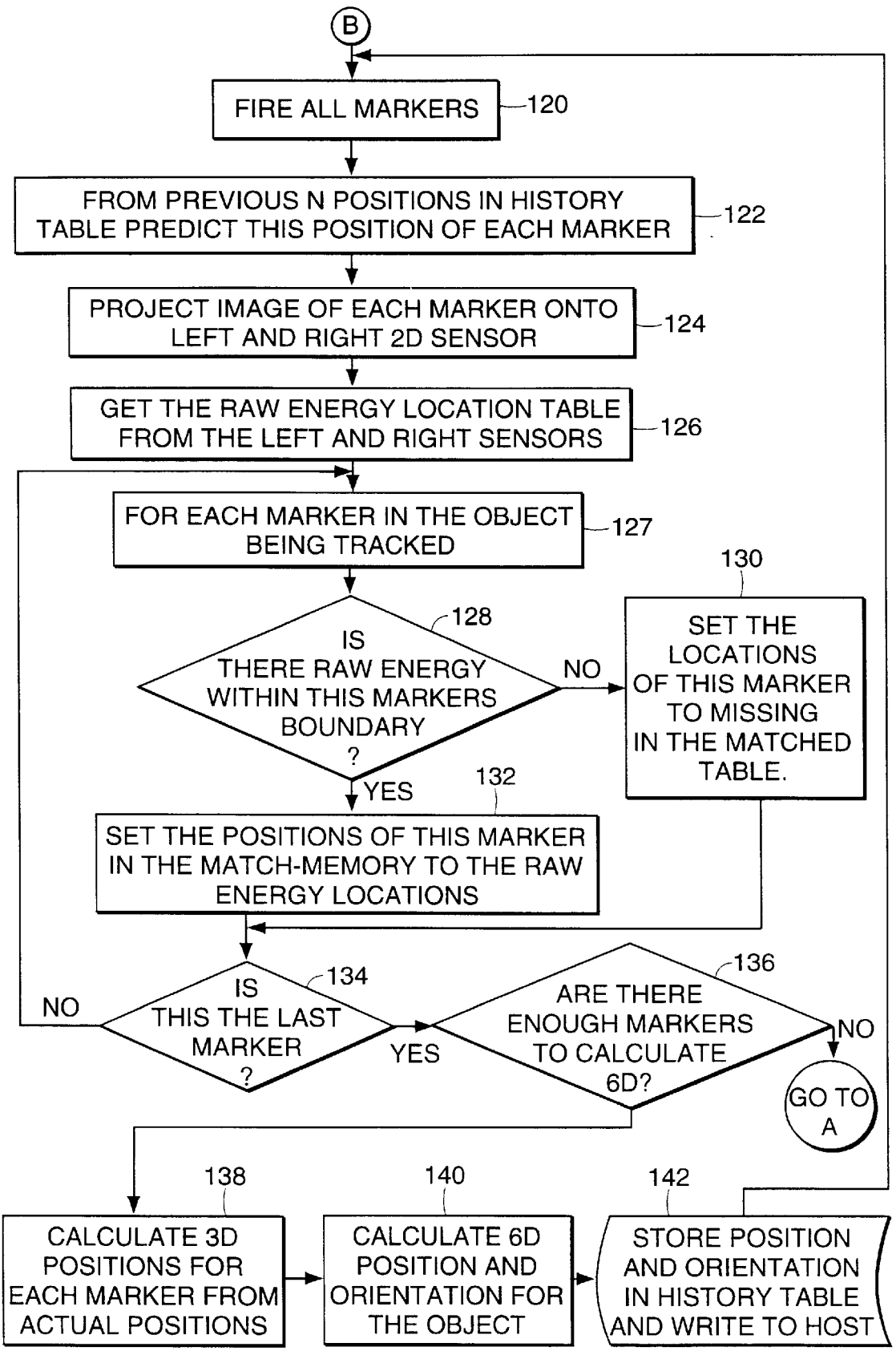

Referring now to FIGS. 10A and 10B, a flow diagram is shown for determining the position and angular orientation of the body 12 with the system 10 (FIG. 1). FIG. 10A shows the steps used during the marker-identification mode and FIG. 10B shows the steps used during the subsequent marker-tracking mode. Thus, referring first to FIG. 10A, during the start of the marker-identification mode all markers are set in the match-memory 42 to "MISSING" and the marker sequence for the object is obtained (i.e., here the markers 14a–14d are sequenced as discussed above) (Step 101). This starts the marker-identification initialization cycles. Thus, in Step 102 all markers 14a–14d identified in the match-memory 42 are activated (i.e., fired) plus the next marker in the sequence is fired. In Step 103 the RAW ENERGY locations are obtained from the RAW ENERGY memories $40_{left}$, $40_{right}$. In Steps 104 and 105, for each sensor $16_{left}$, $16_{right}$ and for each identified marker 14a–14d in the matched-memory 42 a determination is made as to whether there is RAW ENERGY located within the marker's boundary. If the determination is "NO" this marker is set to "MISSING" in the match-memory 42 (Step 106) and the process proceeds with Step 107, described below. If, on the other hand, the determination is "YES" (Step 105), the marker position in the match-memory 42 is up-dated with the true RAW ENERGY centroid position (Step 105b). A determination is made as to whether this is the last marker identified in the match-memory 42 (Step 107). If it isn't, the process returns to Step 104; if on the other hand a determination is made as to whether there is a single additional RAW ENERGY location not yet matched (Step 108). If the determination is "YES" the location of this energy is stored in the next marker sequence position in the match-memory 42 (Step 109). On the other hand, if the determination is "NO" the marker sequencer and controller 28 sequences to the next marker 14a–14d for activation (Step 110). Next, whether the location was stored in the matched table memory in Step 109 or whether the marker sequencer and controller 28 advanced to the next sequential marker 14a–14d, a determination is made as to whether 3 of the 4 markers 14a–14d have been identified on both sensors $16_{left}$, $16_{right}$ (Step 111). If a "NO" determination is made, the process returns to Step 102. If on the other hand, the determination in Step 111 is "YES" the 3D positions for each marker is calculated from actual location data (Step 112). Next, 6D position and angular orientation for the object 12 are calculated (Step 114). Next the calculated position and angular orientation data are stored in HISTORY TABLE memory 45 (Step 116). A determination is then made as to whether more than two positions have been stored in the HISTORY TABLE memory 45 (Step 118). If the determination is "NO" the process returns to Step 102. If on the other hand the determination is "YES" the process proceeds to the marker-tracking mode (FIG. 10B).

Referring now to FIG. 10B. During the marker-tracking mode all markers 14a–14d are activated (i.e., fired) (Step 120). From the previous M positions in the HISTORY TABLE memory 45 a prediction is made for the next position of each marker 14a–14d (Step 122). The image of each marker 14a–14d is mathematically projected onto the two sensors $16_{left}$, $16_{right}$ U, v coordinate system (Step 124). Next, the energy positions are obtained from the RAW ENERGY memories $40_{left}$, $40_{right}$ (Step 126). For each marker a determination is made as to whether there is RAW ENERGY within that marker's boundary (Steps 127 and 128). If the determination is "NO" the location of this marker is set to "MISSING" in the match-memory 42 and the process returns to Step 126 (Step 130). If on the other hand the determination in Step 128 is "YES" the position of this marker is set in the match-memory 42 to the raw energy location (Step 132). Next a determination is made as to whether the marker is the last marker in the sequence (Step 134). If the determination in Step 134 is "NO" the process returns to Step 126. If on the other hand the determination in Step 134 is "YES" a determination is made as to whether there are enough markers identified to calculate 6D (Step 136). If the determination in Step 136 is "NO" the marker-identification phase is re-instituted and the process returns to Step 101 as discussed above in connection with FIG. 10A. If on the other hand the determination in Step 136 is "YES" the 3D positions are calculated for each marker from actual position data (Step 138). Next the 6D position and angular orientation of the object is calculated (Step 140). Next the calculated 6D position and angular orientation is stored in the HISTORY TABLE memory 45 (Step 142) and the marker-tracking mode continues for as long as desired.

Referring to FIG. 11, it is noted that the system 10 produces a determination of the position and angular orientation of the body 12 at the sensor $16_{left}$, $16_{right}$ cycle rate. That is, a position and angular orientation (i.e., a body 12 pose) calculation is made and displayed at sensor cycles m, m+1, m+2 . . . , as indicated in FIG. 11; i.e., each body 12 pose (FIG. 12) is calculated and displayed at each sensor cycle, albeit that the pose calculated and displayed in cycle m+2 is a result of the markers 14a–14d being fired during cycle m. Therefore, the system 10 calculates and displays body 12 poses in real-time.

Figure 13:
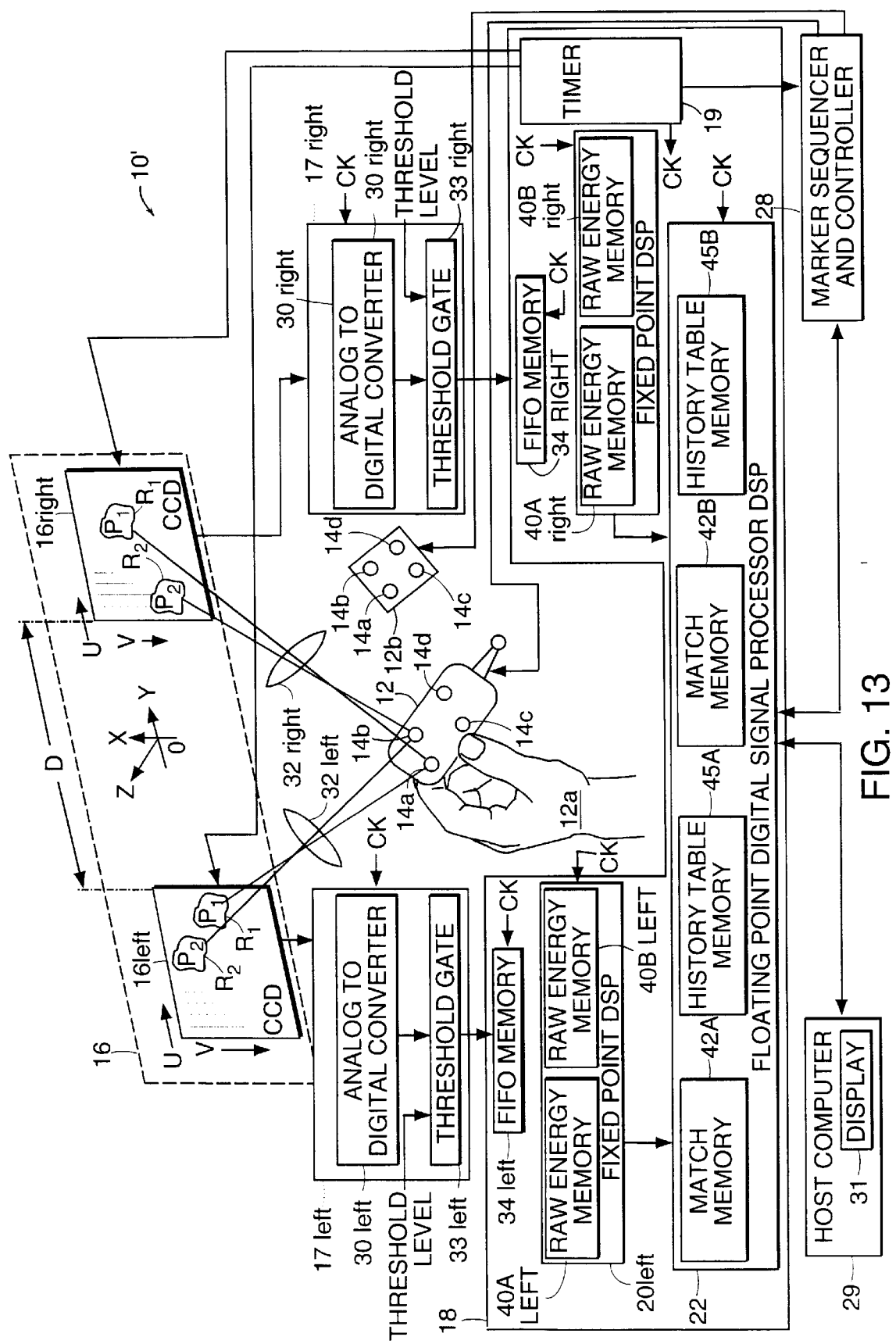
FIG. 13 is a block diagram of a system for determining the spatial position and orientation of a plurality of rigid bodies according to the invention.

While the determination of the position and angular orientation of one rigid body has been described, the determination of the position and angular orientation of more than one rigid body may be obtained by using the system and process described on a sensor cycle time-shared basis for each of the rigid bodies. For example, referring to FIG. 13, a system 10' is shown for determining the position and angular orientation of a plurality of, here two, rigid bodies 12a, 12b. It is first noted that each of the fixed point DSPs $20_{left}$, $20_{right}$ includes a plurality of, here two, RAW ENERGY memories $40a_{left}$, $40b_{left}$, and $40a_{right}$, $40b_{right}$, respectively, as shown. RAW ENERGY memories $40a_{left}$, $40a_{right}$ store the RAW ENERGY data for object 12a and RAW ENERGY memories $40b_{left}$, $40b_{right}$ store the RAW ENERGY data for object 12b. Further, the floating point DSP 22 includes a plurality of, here two, match-memories 42a, 42b and a plurality of, here two HISTORY TABLE memories 45a, 45b. Match-memory 42a provides data matching the RAW ENERGY data associated with body 12a and 2D sensor $16_{left}$, $16_{right}$ positional data of the markers 14a–14d on body 12a while match-memory 42b provides data matching the RAW ENERGY data associated with body 12b and 2D sensor $16_{left}$, $16_{right}$ positional data of the markers 14a–14d on body 12b. HISTORY TABLE memory 45a stores the real-tire poses of body 12a while HISTORY TABLE memory 45b stores the real-time poses of body 12b. Referring now to FIG. 14, it is noted that the system 10' (FIG. 13) produces a determination of the position and angular orientation of the body 12a at the sensor $16_{left}$, $16_{right}$ cycle rate divided by the number of rigid bodies, here 2. That is, a position and angular orientation (i.e., a body 12a pose, FIG. 15) calculation is made and displayed at sensor cycles m, m+2, . . . , as indicated in FIG. 14; i.e., each body 12a pose is calculated and displayed at every other sensor cycle, albeit that the pose calculated and displayed in cycle m is a result of firing markers 14a–14d of body 12a during cycle m−2 (not shown) and a position and angular orientation (i.e., a body 12b pose, FIG. 15) calculation is made and displayed during sensor cycles m+1, m+3 (not shown), . . . , as indicated in FIG. 14; i.e., each body 12b pose is calculated and displayed at every other sensor cycle, albeit that the pose calculated and displayed in cycle m+1 is a result of markers 14a–14d being fired at cycle m−1, not shown. Therefore, the system 10' calculates and displays both body 12a and body 12b poses in real-time.

Other embodiments are within the spirit and scope of the appended claims. For example, while the determination of the location of at least three of the markers 14a–14d is required for 6D position and angular orientation determination, if less than a six degrees of freedom (6D) determination is desired (i.e., a position of, and a vector along, the object 12) the determination of the location of only two of the markers 14a–14d is required. Further, while the sensor section 16 described above included a pair of spaced 2D sensors $16_{left}$, $16_{right}$, such sensor section 16 may include other sensor arrangements. For example, the sensor section 16 may include a single 2D sensor, a pair of linear sensors, or other suitable arrangement of sensors.

What is claimed is:

1. A system for determining the spatial position and angular orientation of an object, comprising:

a plurality of activatable markers adapted for mounting to the object;

a sensor section adapted to detect energy emitted by the markers;

a processor, responsive to signals produced by the sensor section in response to the energy detected by such sensor section, for determining the position of the detected energy on such sensor section;

a controller for activating the markers in a predetermined sequence during a marker-identification mode and for simultaneously activating a plurality of the markers during a subsequent marker-tracking mode;

and wherein the processor matches the determined position of the detected energy with a corresponding one of the markers during the marker-identification mode and tracks the position of each of the simultaneously activated and identified markers during the marker-tracking mode and, wherein the controller sequentially activates a successively increasing number of the plurality of markers during each of one of a corresponding sequence of sensor cycles during the marker-identification mode.

2. The system recited in claim 1 wherein the processor determines the position of the detected energy of an activated first one of the markers during a first cycle of the sensor section during the marker-identification mode and determines the position of an activated second one of the markers during a second cycle of the sensor section while tracking the position of the activated first one of the markers during the marker-identification mode.

3. The system recited in claim 2 wherein the processor tracks the positions of the simultaneously activated first and second markers during the marker-tracking mode.

4. The system recited in claim 1 wherein the processor: determines the position of the detected energy of an activated first one of the markers during a first cycle of the sensor section during the marker-identification mode; determines the position of an activated second one of the markers during a second cycle of the sensor section while tracking the position of the activated first one of the markers during the marker-identification mode; and determines the position of an activated third one of the markers during a third cycle of the sensor section while tracking the position of the activated first and second ones of the markers during the marker-identification mode.

5. The system recited in claim 4 wherein the processor tracks the positions of the simultaneously activated first, second and third markers during the marker-tracking mode.

6. A method for determining the spatial position and angular orientation of an object with a system comprising: a plurality of activatable markers adapted for mounting to the object; a sensor section adapted to detect energy emitted by the markers; and a controller for activating one or more of the markers in a predetermined sequence during a marker-identification mode and for simultaneously activating a plurality of the markers during a subsequent marker-tracking mode, such method comprising the steps of:

determining the position of the detected energy of an activated first one of the markers during a first cycle of the sensor section during the marker-identification mode; and determining the position of an activated second one of the markers during a second cycle of the sensor section while tracking the position of the activated first one of the markers during the marker-identification mode.

7. The system recited in claim 6 including the step of tracking the positions of the simultaneously activated first and second markers during the marker-tracking mode.

8. The system recited in claim 6 including the step of determining the position of an activated third one of the markers during a third cycle of the sensor section while tracking the position of the activated first and second ones of the markers during the marker-identification mode.

9. The system recited in claim 8 including the step of tracking the positions of the simultaneously activated first, second and third markers during the marker-tracking mode.

10. The method recited in claim 6 including the step of estimating the position of one of the markers using a prior knowledge of the spatial relationship among the markers when such one of the markers is obscured from the sensor section.

* * * * *